US00PP19766P2

(12) United States Plant Patent
Dudek

(10) Patent No.: US PP19,766 P2
(45) Date of Patent: Feb. 24, 2009

(54) APPLE TREE NAMED 'DUDEK'

(50) Latin Name: *Malus domestica*
Varietal Denomination: Dudek

(76) Inventor: Britt F. Dudek, 811 Van Well Ave. SE., East Wenatchee, WA (US) 98802

( * ) Notice: Subject to any disclaimer, the term of this patent is extended or adjusted under 35 U.S.C. 154(b) by 0 days.

(21) Appl. No.: 11/803,013

(22) Filed: May 10, 2007

(51) Int. Cl.
*A01H 5/00* (2006.01)

(52) U.S. Cl. ..... Plt./161
(58) Field of Classification Search ..... Plt./161
See application file for complete search history.

(56) References Cited

PUBLICATIONS

Internet website (retrieved Apr. 7, 2008); http://www.all-aboutapples.com/varieties/var_c1.htm#cameo(caudlecv )(2 pages total).*

* cited by examiner

*Primary Examiner*—Annette H Para
*Assistant Examiner*—S. B McCormick Ewoldt
(74) *Attorney, Agent, or Firm*—Stratton Ballew P.C.

(57) ABSTRACT

Apple tree 'DudeK' (*Malus domestica*) is a limb sport mutation of 'Caudle' (PP9,068). The fruit of 'DudeK' is notable for its attractive, intensely colored skin.

3 Drawing Sheets

Genus and species: *Malus domestica.*
Variety denomination: 'Dudek'.

BACKGROUND OF THE INVENTION

The new variety named 'DudeK' is a limb mutation from a tree of the 'Caudle' apple variety (P#9068) on M-7 rootstock planted in my orchard at East Wenatchee, Wash. in 1994. I discovered 'DudeK' as a mutated limb, which was distinguished from other limbs on the tree by its more intensely colored fruit, in September 1998. Upon discovery I took buds of 'Dudek' and top-budded two additional trees on M-7 in the same orchard block. In December of 1999 I grafted buds from the second-generation branches of 'DudeK' onto fourteen five-year-old 'Caudle' trees that were growing on M-7. In August 2001 I budded thirteen M-7 rootstocks with 'Dudek' buds taken from third generation trees in my nursery, and I planted the resulting trees in my orchard in the spring of 2003. All of these trees have fruited, and they consistently carry the early and intense coloring characteristics of the mutation through three generations.

SUMMARY OF THE TREE

The new variety is compared to the parent tree, 'Caudle' variety (PP#9068). It is similar in all respects to the 'Caudle' apple except in the development of red skin color. The drawings and data presented clearly document this difference.

BRIEF DESCRIPTION OF THE PHOTOGRAPHS

Figure 1:
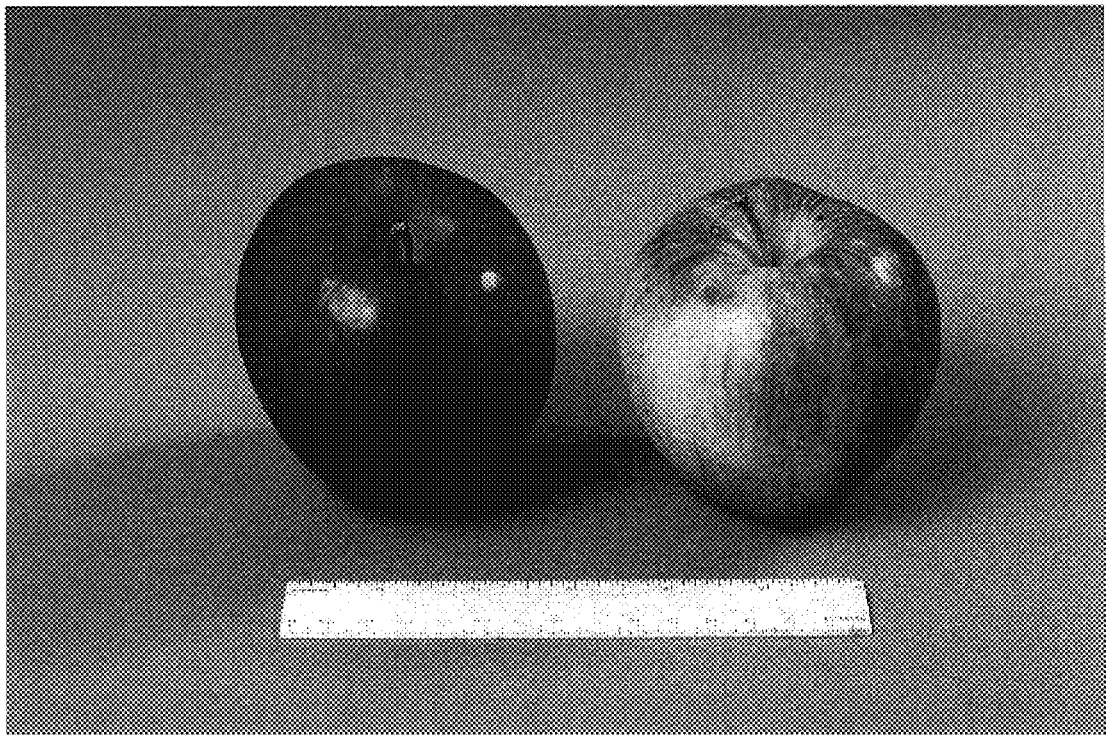
FIG. 1 shows a 'DudeK' apple (left) as compared with a 'Caudle' apple (right)
Figure 2:
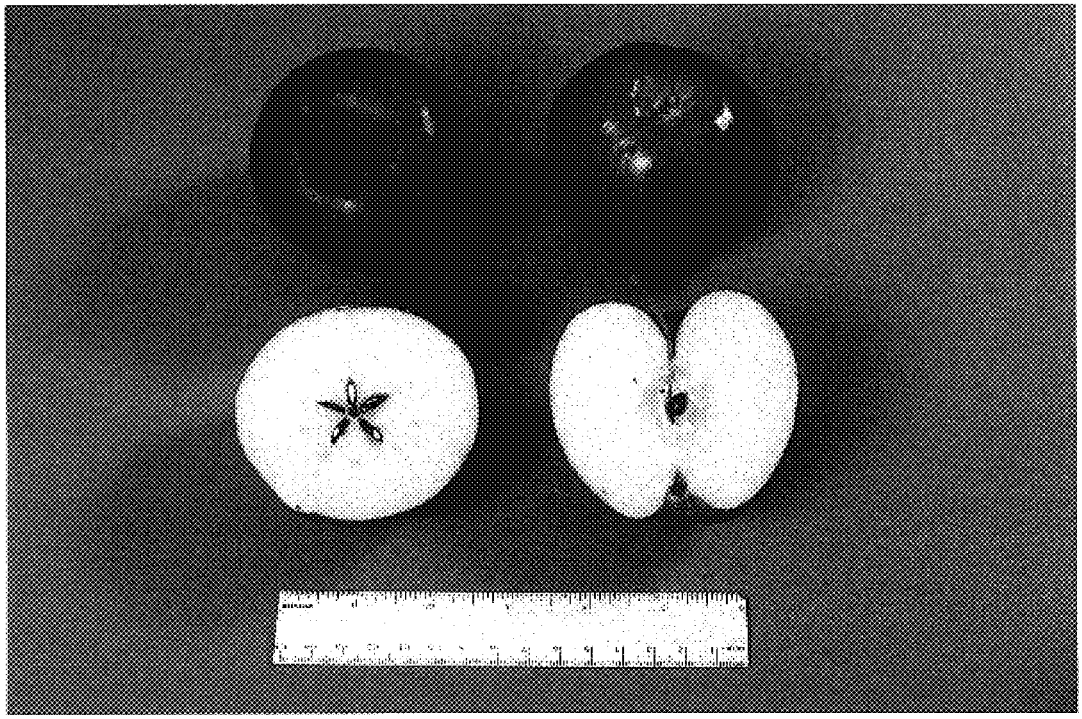
FIG. 2 shows various aspects of the 'DudeK' apple.
Figure 3:
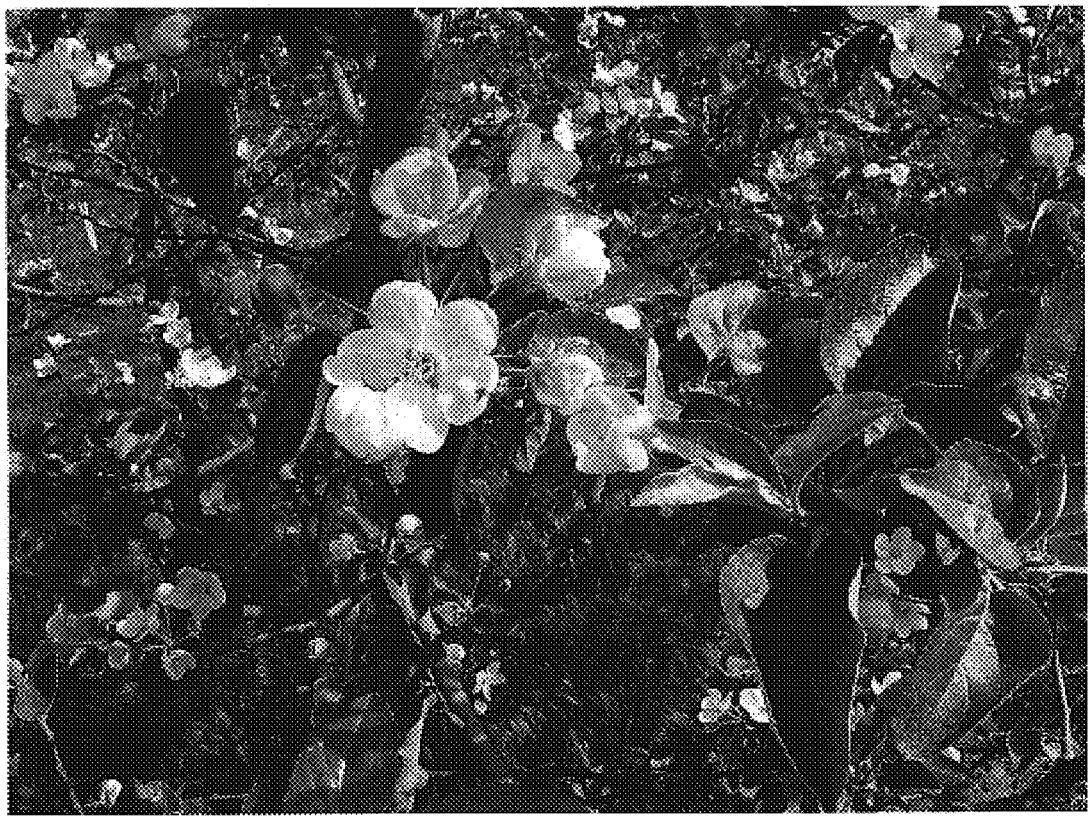
FIG. 3 shows blossoms and leaves of a 'DudeK' apple tree.

The colors of this illustration may vary with lighting conditions and, therefore, color characteristics of this new variety should be determined with reference to the observations described herein, rather than from these illustrations alone.

DETAILED BOTANICAL DESCRIPTION

The following detailed description of the characteristics of 'Dudek', a limb sport mutation of the 'Caudle' variety, is based on observations at East Wenatchee during the 2006 and 2007 growing seasons of trees planted in 2003. The observed tree, limb, and leaf characteristics of the new variety are essentially identical to the parent 'Caudle' variety. All color descriptions by number citations herein (hue/value/chroma) refer to the Munsell Book of Color, Kollmorgen Instruments Corp., 405 Little Britain Road, New Windsor, N.Y. 12553. Certain characteristics of this variety may change with changing environmental conditions (e.g., light, temperature, moisture), nutrient availability, or other factors. Quantified measurements are expressed as an average of measurements taken from a number of individual plants of the new variety. The measurements of any individual plant, or any group of plants, of the new variety may vary from the stated average.

Tree:

*Height.*—Approximately 3 m.
*Width.*—1.5 to 1.8 m.
*Habit.*—Upright to somewhat spreading
*Vigor.*—Medium (30 to 45 cm annual growth), upright to spreading. Mutated branch shows no difference in growth from other branches.
*Productivity.*—Similar to that of 'Caudle'.
*Chilling requirements.*—Similar to 'Caudle', approximately 1000 to 1200 hours.

Trunk:

*Size.*—Diameter 15 cm at one foot above ground.
*Trunk bark texture.*—Smooth on younger wood, becoming flaking with age.
*Trunk bark color.*—Brown, with grayish bloom (5 YR 6/2).

Branches:

*Habit.*—Branches on original, mutated branch are upright to spreading; average branch angle is 60 degrees.

*Size and texture.*—Approximately 5 cm diameter at base; smooth texture.
*Branch color.*—Reddish brown (7.5 R 3/4).
*Branch pubescence.*—Glabrous.
*Branch lenticels.*—Sparse, small.
*Internodes.*—5 cm.

Leaves (primary):
*Length.*—93 mm.
*Width.*—70 mm.
*Form.*—Ovate.
*Margin.*—Crenate.
*Tip.*—Acute to acuminate.
*Base.*—Obtuse.
*Leaf color.*—Upper surface medium green (2.5 GY 6/6); lower surface light green (2.5 GY 7/4).
*Pubescence.*—Upper surface glabrous; lower surface almost glabrous with fine pubescence along midrib; pubescence colorless.
*Vein color.*—Primary veins purple (7.5 RP 3/10).
*Venation pattern.*—Alternate lateral venation.
*Petiole.*—Average 28 mm to base of leaf blade; diameter 2 mm; color of petiole is 7.5 RP 3/10).
*Stipules.*—In pairs, thin, pointed; length 10 to 12 mm, width 2 to 3 mm.

Flowers: Similar, if not identical to 'Caudle'.
*Bud.*—Round to oval, length 10 mm, diameter 5 mm.
*Bloom.*—First bloom April 27; Full bloom May 2; Bloom duration 7 days (during 2007 growing season in East Wenatchee, Wash.
*Flower size.*—Medium-large, diameter 45 to 55 mm.
*Flower color.*—Pink (10 RP 6/6) in popcorn stage; white when fully open.
*Petals.*—Quantity 5; rounded at apex, obtuse at base; smooth margin and texture; margins touching to overlapping by 10%.
*Stamen.*—Single row, anthers bright yellow (2.5 Y 8.5/12).
*Pistil.*—Style medium length, branched into 5 elements; stigma round.
*Filament.*—Quantity 15; length 10 mm.
*Sepals.*—Quantity 5; length 8 mm, width at base 4 mm; pubescent, recurved downward, pale green (10 GY 7/2).
*Peduncle.*—Length 25 to 40 mm, thickness 1 to 2 mm; pale green (10 GY 7/2).
*Pollination requirements.*—Identical to 'Caudle', i.e. compatible with all diploid cultivars except 'Caudle'.
*Fragrance.*—Medium to strong apple fragrance.

Fruit: (Maturity when described was mid- to late-harvest period, Oct. 17, 2006).
*Firmness.*—Sixteen pounds pressure as measured by penetrometer.
*Soluble solids.*—14.3%.
*Starch index.*—5.5 (1 to 6 scale).
*Acid content.*—0.45% malic acid.
*Storage.*—Similar to 'Caudle'; excellent keeping quality.
*Size.*—Large, transverse diameter 80 to 95 mm, length 70 to 95 mm; 254 g.
*Form.*—Conic, symmetric; length/diameter ratio approximately 1:0.9; no ribbing; 5 lobes at calyx end, lobes less prominent than those on 'Red Delicious'.
*Stem cavity.*—Medium to broad, depth 21 mm.
*Basin cavity.*—Depth medium, 10 mm; Width medium to wide, 37 mm, lightly pubescent.
*Stem.*—Length medium to long, 15 to 35 mm; thickness medium, 2 to 5 mm.
*Locules (carpels).*—Large; quantity 5; closed, with seeds attached, 1 to occasionally 2 seeds per locule.
*Skin.*—Thin, tender, glossy; no tendency to become oily in storage, not prone to russet; occasional cracking around stern cavity with advanced maturity.
*Lenticels.*—Large, 1 mm; round, conspicuous; yellow (5 Y 8/6).
*General color effects.*—Combination of striped and blushed red color over 90% to 100% of the fruit surface, as contrasted with 'Caudle' apple, which has 40% to 60% red color.
*Ground color.*—Yellow when fully mature (5 Y 8/10), but rarely observed, and then in basin of shaded fruit only. Most fruit are totally colored with red.
*Over color.*—Prominent dark red stripes (7.5 R 3/10) of variable width over carmine red blush (7.5 R 4/14).
*Russet.*—Absent
*Flesh.*—Color cream (5 Y 9/4); very crisp, juicy, and sweet; non astringent, low acidity; very firm at prime harvest, 16 to 20 pounds, remaining firm at long storage.
*Flavor.*—Sweet, identical to that of 'Caudle'.
*Acidity.*—Medium; more acid than 'Red Delicious', less than 'Braeburn'.
*Aroma.*—Faint.
*Core.*—Width 25 mm, length 31 mm; 10 bundles, bundle area round; core lines prominent; locules closed; calyx tube closed, length medium, 10 mm.
*Seeds.*—Mostly 1 per cell; obovate; color dark reddish brown (10 R 2/6); length 8 mm, width 5 mm; unattached to carpel wall at prime maturity.
*Use.*—Primarily dessert.

Disease and pest resistance/susceptibility: Same as parent

Drought and heat tolerance: Fruit is susceptible to sunburn in north central Washington state, but can otherwise withstand typical climatic extremes.

It is claimed:

1. I claim a new and distinct apple tree as shown and described herein.

* * * * *